US010178990B2

(12) United States Patent
Kim

(10) Patent No.: US 10,178,990 B2
(45) Date of Patent: Jan. 15, 2019

(54) APPARATUS FOR INSERTING SURGICAL THREAD, AND SURGICAL PROCEDURE KIT FOR INSERTING SURGICAL THREAD COMPRISING SAME

(71) Applicant: Y. JACOBS MEDICAL INC., Seoul (KR)

(72) Inventor: Young Jae Kim, Seoul (KR)

(73) Assignee: Y. Jacobs Medical Inc., Seoul (KR)

( * ) Notice: Subject to any disclaimer, the term of this patent is extended or adjusted under 35 U.S.C. 154(b) by 413 days.

(21) Appl. No.: 14/648,070

(22) PCT Filed: Dec. 5, 2013

(86) PCT No.: PCT/KR2013/011239
§ 371 (c)(1),
(2) Date: May 28, 2015

(87) PCT Pub. No.: WO2014/088353
PCT Pub. Date: Jun. 12, 2014

(65) Prior Publication Data
US 2015/0305736 A1    Oct. 29, 2015

Related U.S. Application Data

(63) Continuation-in-part of application No. 13/706,108, filed on Dec. 5, 2012.

(51) Int. Cl.
A61B 17/04    (2006.01)
A61B 17/06    (2006.01)
A61B 17/00    (2006.01)

(52) U.S. Cl.
CPC ...... A61B 17/0482 (2013.01); A61B 17/0469 (2013.01); A61B 17/06004 (2013.01);
(Continued)

(58) Field of Classification Search
CPC .......... A61B 17/06166; A61B 17/0401; A61B 2017/0496; A61B 2017/0412;
(Continued)

(56) References Cited

U.S. PATENT DOCUMENTS 3,123,077 A    3/1964 Alcamo
3,981,307 A    9/1976 Borysko
(Continued)

FOREIGN PATENT DOCUMENTS

CN    101219066 A    7/2008
CN    2012166619 Y    4/2009
(Continued)

OTHER PUBLICATIONS

BD Product Catalog, Jan. 2010, BD Medical.
(Continued)

Primary Examiner — Christopher L Templeton
Assistant Examiner — Mikail Mannan
(74) Attorney, Agent, or Firm — Knobbe Martens Olson & Bear, LLP

(57) ABSTRACT

A medical thread insertion surgery kit includes an insertion path forming unit which includes a pipe member comprising a pipe that is hollow and forms a path through which a medical thread is to be inserted and a support member comprising a support rod that is inserted into the pipe of the pipe member and has stiffness greater than stiffness of the pipe member; a medical thread supply unit which supplies a medical thread through the pipe member after the support member is removed from the insertion path forming unit; and a push unit that is slidable in the pipe of the pipe member and pushes the medical thread through the pipe of the pipe member.

5 Claims, 18 Drawing Sheets

(52) U.S. Cl.
CPC ............ *A61B 17/06166* (2013.01); *A61B 2017/00792* (2013.01); *A61B 2017/06042* (2013.01); *A61B 2017/06052* (2013.01); *A61B 2017/06176* (2013.01)

(58) Field of Classification Search
CPC .... A61B 2017/0427; A61B 2017/0458; A61B 2017/0445; A61B 2017/06171; A61B 2017/06176; A61B 2017/0618; A61B 2017/06185; A61B 17/0469; A61B 17/0483; A61B 17/0482; A61B 2017/0409
See application file for complete search history.

(56) References Cited

U.S. PATENT DOCUMENTS

| | | |
|---|---|---|
| 4,744,364 A | 5/1988 | Kensey |
| 4,805,292 A | 2/1989 | Noguchi |
| 4,922,904 A | 5/1990 | Uetake |
| 4,932,962 A | 6/1990 | Yoon et al. |
| 5,041,129 A | 8/1991 | Hayhurst et al. |
| 5,053,046 A | 10/1991 | Janese |
| 5,053,047 A | 10/1991 | Yoon |
| 5,080,667 A | 4/1992 | Chen et al. |
| 5,192,301 A | 3/1993 | Kamiya et al. |
| 5,207,694 A | 5/1993 | Broome |
| 5,224,955 A | 7/1993 | West |
| 5,236,443 A | 8/1993 | Sontag |
| 5,259,846 A | 11/1993 | Granger et al. |
| 5,269,809 A | 12/1993 | Hayhurst et al. |
| 5,306,294 A | 4/1994 | Winston et al. |
| 5,330,503 A | 7/1994 | Yoon |
| 5,500,000 A | 3/1996 | Feagin |
| 5,626,614 A | 5/1997 | Hart |
| 5,643,295 A | 7/1997 | Yoon |
| 5,683,417 A | 11/1997 | Cooper |
| 5,741,299 A | 4/1998 | Rudt |
| 5,931,855 A | 8/1999 | Buncke et al. |
| 6,241,747 B1 | 6/2001 | Ruff |
| 6,939,326 B1 | 9/2005 | Thappa |
| 7,056,331 B2 | 6/2006 | Kaplan et al. |
| 7,468,068 B2 | 12/2008 | Kolster |
| 7,582,105 B2 | 9/2009 | Kolster |
| 7,601,164 B2 | 10/2009 | Wu |
| 7,967,841 B2 | 6/2011 | Yuan et al. |
| 7,988,727 B2 | 8/2011 | Santamore et al. |
| 8,192,462 B2 | 6/2012 | Sulamanidze et al. |
| 8,747,438 B2 | 6/2014 | Longo et al. |
| 8,758,367 B2 | 6/2014 | Philippon et al. |
| 9,044,224 B2 | 6/2015 | Lauria |
| 9,125,647 B2 | 9/2015 | Goraltchouk et al. |
| 9,204,965 B2 | 12/2015 | Longoria |
| 9,675,341 B2 | 6/2017 | D'agostino et al. |
| 2002/0198544 A1 | 12/2002 | Uflacker |
| 2003/0149447 A1 | 8/2003 | Morency et al. |
| 2004/0030319 A1 | 2/2004 | Korkor et al. |
| 2004/0153102 A1 | 8/2004 | Therin et al. |
| 2005/0101984 A1* | 5/2005 | Chanduszko ...... A61B 17/0057 606/185 |
| 2005/0240224 A1 | 10/2005 | Wu |
| 2005/0245963 A1* | 11/2005 | Kida ................ A61B 17/12022 606/200 |
| 2006/0079935 A1 | 4/2006 | Kolster |
| 2006/0135994 A1 | 6/2006 | Ruff et al. |
| 2006/0135996 A1 | 6/2006 | Schwartz et al. |
| 2006/0265010 A1 | 11/2006 | Paraschac et al. |
| 2007/0038249 A1 | 2/2007 | Kolster |
| 2007/0167958 A1 | 7/2007 | Sulamanidze et al. |
| 2007/0213770 A1* | 9/2007 | Dreyfuss .......... A61B 17/06166 606/228 |
| 2008/0058816 A1* | 3/2008 | Philippon .......... A61B 17/0401 606/326 |
| 2008/0132943 A1 | 6/2008 | Maiorino et al. |
| 2008/0228144 A1* | 9/2008 | Liniger ................ A61M 5/158 604/164.08 |
| 2008/0281357 A1 | 11/2008 | Sung et al. |
| 2009/0088797 A1 | 4/2009 | Crombie et al. |
| 2009/0093670 A1 | 4/2009 | Annest et al. |
| 2009/0112259 A1 | 4/2009 | D'Agostino |
| 2009/0210003 A1 | 8/2009 | Sulamanidze et al. |
| 2009/0299407 A1 | 12/2009 | Yuan et al. |
| 2010/0137679 A1 | 6/2010 | Lashinski et al. |
| 2010/0160961 A1 | 6/2010 | Nawrocki et al. |
| 2011/0054522 A1 | 3/2011 | Lindh et al. |
| 2011/0238111 A1 | 9/2011 | Frank |
| 2011/0270304 A1 | 11/2011 | Lee |
| 2011/0282386 A1 | 11/2011 | Friedrich et al. |
| 2011/0288563 A1* | 11/2011 | Gianotti ............ A61B 17/0057 606/144 |
| 2012/0109193 A1 | 5/2012 | Primavera et al. |
| 2012/0109195 A1 | 5/2012 | Odermatt et al. |
| 2012/0239002 A1 | 9/2012 | Griswold |
| 2013/0245684 A1 | 9/2013 | Ruff et al. |
| 2013/0345745 A1 | 12/2013 | Kim |
| 2014/0155913 A1 | 6/2014 | Kim |
| 2014/0228971 A1 | 8/2014 | Kim |
| 2014/0364904 A1 | 12/2014 | Kim |
| 2015/0366553 A1 | 12/2015 | Kim |
| 2016/0302905 A1 | 10/2016 | Kim |

FOREIGN PATENT DOCUMENTS

| | | |
|---|---|---|
| CN | 101500495 A | 8/2009 |
| CN | 102271734 A | 12/2011 |
| DE | 3223153 C1 | 8/1983 |
| DE | 102008057213 A1 | 5/2010 |
| EP | 0314412 A1 | 5/1989 |
| EP | 1929961 A2 | 6/2008 |
| EP | 1955720 A1 | 8/2008 |
| EP | 2020209 A1 | 2/2009 |
| EP | 2108316 A2 | 10/2009 |
| EP | 2386252 A1 | 11/2011 |
| EP | 2386323 A2 | 11/2011 |
| GB | 1091282 A | 11/1967 |
| JP | 04-307050 A | 10/1992 |
| JP | 04-307052 A | 10/1992 |
| JP | 08-52154 A | 2/1996 |
| JP | 08-140982 A | 6/1996 |
| JP | 02-277459 B2 | 5/1998 |
| JP | 10-258123 A | 9/1998 |
| JP | 10-272182 A | 10/1998 |
| JP | 2000-202029 A | 7/2000 |
| JP | 3069906 U | 7/2000 |
| JP | 2000-225118 A | 8/2000 |
| JP | 2000-232984 A | 8/2000 |
| JP | 2002-516585 A | 6/2002 |
| JP | 2003-019683 A | 1/2003 |
| JP | 2004-041492 A | 2/2004 |
| JP | 2004-057516 A | 2/2004 |
| JP | 2004-073403 A | 3/2004 |
| JP | 2004-121634 A | 4/2004 |
| JP | 2004-530524 A | 10/2004 |
| JP | 2004-329964 A | 11/2004 |
| JP | 2005-177499 A | 7/2005 |
| JP | 2005-177500 A | 7/2005 |
| JP | 2006-025867 A | 2/2006 |
| JP | 2006-515203 A | 5/2006 |
| JP | 2007-075616 A | 3/2007 |
| JP | 2007-090062 A | 4/2007 |
| JP | 2007-537017 A | 12/2007 |
| JP | 2008-114074 A | 5/2008 |
| JP | 2008-514382 A | 5/2008 |
| JP | 2008-132327 A | 6/2008 |
| JP | 2008-132328 A | 6/2008 |
| JP | 2008-132329 A | 6/2008 |
| JP | 2008-546454 A | 12/2008 |
| JP | 2009-517156 A | 4/2009 |
| JP | 2009-531071 A | 9/2009 |
| JP | 2009-247890 A | 10/2009 |
| JP | 2009-279393 A | 12/2009 |
| JP | 2010-500102 A | 1/2010 |
| JP | 2010-507453 A | 3/2010 |

(56) References Cited

FOREIGN PATENT DOCUMENTS

| | | |
|---|---|---|
| JP | 2010518902 A | 6/2010 |
| JP | 2010-537676 A | 12/2010 |
| JP | 2011-500208 A | 1/2011 |
| JP | 2011-240133 A | 12/2011 |
| JP | 2011-240134 A | 12/2011 |
| JP | 2012515015 A | 7/2012 |
| KR | 10-0178358 B1 | 4/1998 |
| KR | 20-0287634 Y1 | 8/2002 |
| KR | 20-0320005 Y1 | 7/2003 |
| KR | 10-0473108 B1 | 12/2003 |
| KR | 10-2005-0108494 A | 11/2005 |
| KR | 10-0761921 B1 | 10/2007 |
| KR | 10-2008-0039345 A | 5/2008 |
| KR | 10-2009-0035692 A | 4/2009 |
| KR | 10-2009-0103639 A | 10/2009 |
| KR | 10-1105647 B1 | 8/2010 |
| KR | 10-2010-0120642 A | 11/2010 |
| KR | 20-0451570 Y1 | 12/2010 |
| KR | 10-2011-0019895 A | 3/2011 |
| KR | 10-1044731 B1 | 6/2011 |
| KR | 10-1057376 B1 | 8/2011 |
| KR | 10-2012-0010049 A | 2/2012 |
| KR | 10-1132841 B1 | 4/2012 |
| KR | 10-1155817 B1 | 6/2012 |
| KR | 10-1182337 B1 | 9/2012 |
| KR | 10-1185583 B1 | 9/2012 |
| KR | 10-1326736 B1 | 11/2013 |
| KR | 10-1367902 B1 | 2/2014 |
| KR | 10-1455206 B1 | 10/2014 |
| SU | 700121 A1 | 11/1979 |
| SU | 1178420 A1 | 2/1984 |
| SU | 1360705 A1 | 7/1986 |
| WO | 2007/098212 A2 | 8/2007 |
| WO | 2008/020937 A2 | 2/2008 |
| WO | 2008/057261 A1 | 5/2008 |
| WO | 2008103308 A1 | 8/2008 |
| WO | 2009/027883 A2 | 3/2009 |
| WO | 2009/055105 A1 | 4/2009 |
| WO | 2010/028324 A2 | 3/2010 |
| WO | 2010/052006 A1 | 5/2010 |
| WO | 2010/062743 A | 6/2010 |
| WO | 2010080014 A2 | 7/2010 |
| WO | WO 2010062743 A3 * | 9/2010 ....... A61B 17/06109 |
| WO | 2011/128392 A1 | 10/2011 |
| WO | 2012144677 A1 | 10/2012 |
| WO | 2013/169075 A1 | 11/2013 |
| WO | 2015/083864 A1 | 6/2015 |

OTHER PUBLICATIONS

"Optinova ICM (TM) IV-catheter tubing", 2007, Optimus Nova.
John Jacobs Medical, "Youngs Lift", Jun. 7, 2012.
"Catheter", retrieved from http://ko.wikipedia.org/wiki/%EC%B9%B4%EE%85%8C%ED%84%B0?oldid=13222103 on or before Jan. 13, 2015.
"I.V.Catheter, Product Introduction", http://www.dukwooco.co.kr/english/product/pro_1.htm, Dukwoo Medical Co., LTD., printed on Apr. 9, 2016.
Prado et al., "Supplemental Fixation After Endoscopic Brow Elevation Using a Single Nylon Suture", Printed from QMP's Plastic Surgery Pulse News, 2010, vol. 2, No. 1, Quality Medical Publishing, St. Louis, obtained from http://www.plasticsurgerypulsenews.com/2/article_dtl.php?QnCategoryID=18QnArticleID=45.
"Polydioxanone Suture", Metro Korea, retrieved from http://www.metrokr.com/shop/goods/goods_view.php? goodsno=186785506 &category=004 on or before Oct. 30, 2015.
"Safelock Catheter", LKMedical Co., Ltd. Product Catalog, retrieved from http://www.lkmedical.com on or before Oct. 30, 2015.
"Qosina, Thousands of Stock Components," 2014, Qosina Product Catalog.
"Angiocatheter", retrieved from http://medical-dictionary.thefreedictionary.com/angiocatheter on or before Oct. 2, 2015.
"Food and drug safety—wife medical equipment e-petitions", Ministry of Food and Drug Safety, retrieved from https://www.emed.mfds.go.kr, on or before Nov. 3, 2015.
Office Communication Japanese Patent Office on third party submission of references in Japanese Patent Application 2014-549981 dated Jan. 25, 2016—20 pages.
Photos of BD Inc's Product, produced on Jul. 18, 2006, BD Inc.
"MediFirst Homepage", http://www.medifirst.co.kr, published on Nov. 5, 2013.
Karam et al., "Curved Stylet Core Biopsy Results in Larger Cores", American Journal of Roentgenology, Jul. 2010, vol. 195, pp. 242-244.
Application of related U.S. Appl. No. 15/102,240.
Japanese Office Action dated Jun. 30, 2016 of Japanese Patent Application No. 2014-207825 corresponding to related U.S. Appl. No. 14/003,390—2 pages.
European Office Action dated Jun. 6, 2017 of corresponding European Patent Application No. 13860215.6—5 pages.

* cited by examiner

APPARATUS FOR INSERTING SURGICAL THREAD, AND SURGICAL PROCEDURE KIT FOR INSERTING SURGICAL THREAD COMPRISING SAME

TECHNICAL FIELD

One or more embodiments relate to a medical thread insertion apparatus for use in a procedure in which a medical thread for surgical operation is inserted into the living body and fixed, and a medical thread insertion surgery kit including the medical thread.

BACKGROUND ART

A medical thread has been used for a long time to connect or suture a damaged muscular, vascular, or nervous tissue or a surgically incised tissue. Also, a medical thread is used for a double eyelid surgery or a surgery for removing sagging or wrinkles from a skin or a tissue due to aging, reduced skin elasticity, external wound, overuse, or necrosis. A lift surgery lifts up a loose skin or tissue and removes wrinkles on a face, jaw, neck, abdomen, vagina, breast, or hip by using a medical thread and a needle instead of knives. The lift surgery does not require excessive incision, minimizes scars, and causes slight bleeding and swelling. Due to such features, the lift surgery is highlighted.

However, in a conventional lift surgery using a medical thread, in order to insert and fix the medical thread into a body, one insertion through-hole is formed at a point of the body into which the medical thread is inserted and at least one fixed through-hole is formed at a point of the body to which the medical thread is fixed, the medical thread is inserted through the insertion through-hole, is pushed from behind such that a front end portion of the medical thread passes through the fixed through-hole to stick out of the fixed through-hole, and is knotted, and then a skin with the knot is sutured or a skin incision is closed.

However, since the medical thread passes through the insertion through-hole to be inserted into the skin, passes through the fixed through-hole to be discharged from the body, and then is inserted into the body to be fixed, the conventional lift surgery has problems in that a plurality of through-holes have to be formed, it is difficult to insert the medical thread into the body, it takes a lot of time to perform the conventional lift surgery, and there is a high risk because of a high level of anesthesia.

DETAILED DESCRIPTION OF THE INVENTION

Technical Task to Solve

The basic objective of the present invention is to overcome the above-mentioned problems of the prior art. Specifically, according to embodiments of the present invention, inserting of a medical thread into the tissue of living body may be easily performed, a physical wound may less remain in the living body, the inserting of a medical thread may require less time, and the medical thread may be inserted to a predetermined position and strongly fixed.

According to another aspect of the present invention, provided is an apparatus for a lift surgery in which a medical thread is inserted into the tissue of living body to lift up a loose skin and tissue of the living body and to remove wrinkles, and a kit therefor.

Technical Solution

According to an aspect of the present invention, a medical thread insertion apparatus includes an insertion path forming unit which includes a pipe member including a pipe that is hollow and forms a path through which a medical thread is to be inserted and a support member including a support rod that is inserted into the pipe of the pipe member and has stiffness greater than stiffness of the pipe member; and a medical thread supply unit which supplies a medical thread through the pipe member after the support member is removed from the insertion path forming unit.

An inclined insertion unit which is tapered may be formed on an outer surface of an end portion of the pipe member.

According to an embodiment of the present invention, a two-step inclined portion which is tapered at an angle greater than an angle of the inclined insertion unit may be formed on an end portion of the inclined insertion unit.

According to an embodiment of the present invention, the inclined insertion unit may further include at least one cut line that is formed in parallel to an axial direction of the pipe member to branch the end portion of the pipe member.

The pipe member may include a coupling unit including a mount groove that is hollow and tapered and receives the medical thread supply unit therein, and the medical thread supply unit includes a medical thread retaining unit including a supply pipe that is hollow and retains the medical thread to be inserted therein, wherein the medical thread retaining unit includes a connector having a complementary shape to the mount groove of the pipe member, wherein the medical thread retaining unit is coupled to the mount groove via the connector.

A medical thread support for fixing the medical thread in the tissue of the living body may be formed on an end portion of the medical thread.

The medical thread may have a loop shape and the medical thread support is disposed at a position where both ends of the medical thread are adjoined.

The medical thread support may have a truncated cone shape whose diameter increases away from a side where the medical thread is inserted toward an opposite side.

A diameter of an end portion of the medical thread at the side where the medical thread is to be inserted may be greater than that of an opposite end portion of the medical thread.

The medical thread may include barbs that obliquely protrude toward an end portion of the medical thread at a side where the medical thread is inserted.

A maximum diameter of the medical thread support may be the same as or less than an inner diameter of the supply pipe.

A shoulder portion that protrudes inward in a radial direction may be formed on an inner surface of the mount groove.

In the medical thread insertion apparatus according to an embodiment of the present invention, the pipe member includes a coupling unit including a mount groove that is hollow and tapered and receives the medical thread supply unit therein, and the medical thread supply unit includes the medical thread and a medical thread support that is formed on an end portion of the medical thread and fixes the medical thread in the tissue of the living body.

According to another aspect of the present invention, a medical thread insertion surgery kit includes: an insertion path forming unit which includes a pipe member including a pipe that is hollow and forms a path through which a medical thread is to be inserted and a support member including a support rod that is inserted into the pipe of the pipe member and has stiffness greater than stiffness of the pipe member; and a medical thread supply unit which supplies a medical thread through the pipe member after the support member is removed from the insertion path forming unit; and a push unit that is slidable in the pipe of the pipe member and pushes the medical thread through the pipe of the pipe member.

The insertion path forming unit may further include a through-hole forming unit for forming a through hole in a tissue of a living body.

The push unit may include a push rod that has a length great enough to pass through and escape from the insertion path forming unit and the medical thread supply unit.

Advantageous Effects

A medical thread insertion apparatus and a medical thread insertion surgery kit including the same, according to the above-mentioned embodiments of the present invention, may produce following effects.

First, since a support fixed to the tissue of the living body is formed on a medical thread that is inserted, and thus only a through-hole for inserting an end portion of the medical thread into the tissue of the living body needs to be formed in the tissue of the living body, damage to the tissue of the living body may be reduced.

Second, since a surgery for preventing wrinkles of a skin may end only by inserting the medical thread into one through-hole, the surgery may be simplified.

Third, since an end portion of an insertion path forming unit for inserting the medical thread into a through-hole is tapered such that the medical thread may pass through the insertion path forming unit and the end portion of the insertion path forming unit may be easily introduced into the tissue of the living body, frication during introduction into the tissue of the living body may be reduced.

Fourth, a pipe member of the insertion path forming unit into which the medical thread is inserted is flexible and thus may not easily move in the tissue of the living body. However, since the insertion path forming unit moves forward in the tissue of the living body in a state where a support member having stiffness greater than that of the pipe member is inserted into the pipe member, an insertion path may be easily formed.

Fifth, since a frictional force applied when the insertion path forming unit is introduced may be further reduced by forming a tapered two-step inclined portion that is tapered at an angle greater than that of an inclined insertion unit on the inclined insertion unit that is formed on an end portion of the insertion path forming unit, a surgery may be facilitated.

Sixth, since a cut line is formed on an end portion of the inclined insertion unit, the medical thread on which the support for supporting the medical thread at a predetermined point in the tissue is formed may be easily separated from the inclined insertion unit.

Seventh, since an additional push unit is provided such that the medical thread whose stiffness is not sufficient may be introduced into the tissue of the living body, the medical thread may be introduced into the tissue of the living body without difficulty with the help of the push unit.

Eighth, since a medical thread supply unit may be inserted into the pipe member after an insertion path of the medical thread is formed and thus the medical thread does not interfere when the insertion path is formed, the insertion path may be easily formed and damage to the medical thread may be avoided.

Ninth, since an operation of inserting the medical thread is facilitated, a total time taken to perform the operation of inserting the medical thread may be reduced.

Tenth, the medical thread may be inserted into a predetermined position of the tissue of the living body and may be firmly fixed to the predetermined position.

Eleventh, since the medical thread which may lift up the tissue is inserted into the living body, a loose skin or tissue may be lifted and wrinkles may be removed.

BEST MODE

Figure 1:
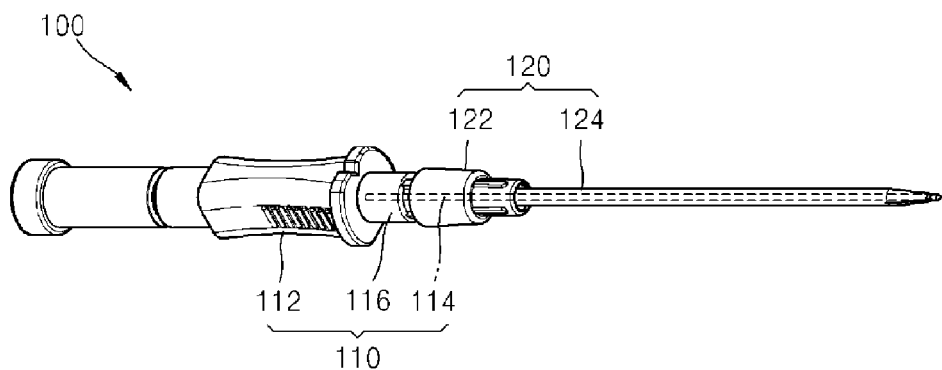
FIG. 1 is a perspective view illustrating an insertion path forming unit which is assembled, according to an embodiment of the present invention.

The present invention will now be described more fully with reference to the accompanying drawings, in which exemplary embodiments of the invention are shown. In the drawings, sizes of specific portions may be exaggerated for clarity. Accordingly, relative proportions of sizes of elements are not limited to those in the drawings of the present invention.

A medical thread insertion surgery kit according to an embodiment of the present invention includes a medical thread insertion apparatus that includes an insertion path forming unit for forming a path along which a medical thread is introduced, a medical thread supply unit for supplying a medical thread, a push unit that pushes the medical thread from behind by sliding in the insertion path forming unit, and optionally, a through-hole forming unit for punching a skin tissue of the living body into which the medical thread is to be inserted.

Figure 2:
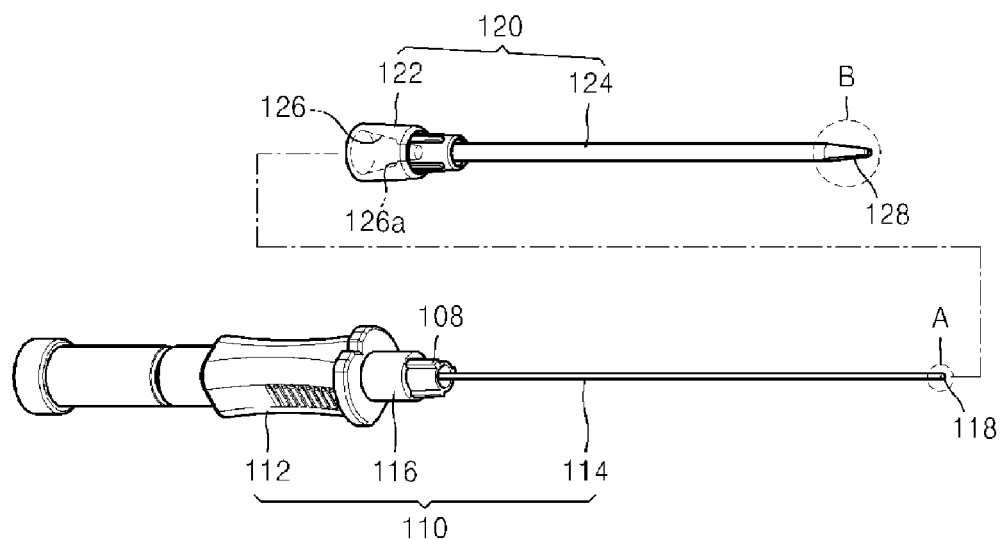
FIG. 2 is an exploded perspective view illustrating the insertion path forming unit of FIG. 1.

FIG. 1 is a perspective view illustrating an insertion path forming unit 100 which is assembled, according to an embodiment of the present invention. FIG. 2 is an exploded perspective view illustrating the insertion path forming unit 100 of FIG. 1.

Referring to FIGS. 1 and 2, the medical thread insertion apparatus includes the insertion path forming unit 100 including: a pipe member 120 including a hollow pipe 124 that forms an insertion path; and a support member 110 including a support rod 114 that is inserted into the pipe 124 of the pipe member 120 and has stiffness greater than that of the pipe member 120.

Since the pipe member 120 of the insertion path forming unit 100 moves forward in a tissue of the living body, the pipe member 120 is formed of an elastic material having predetermined flexibility in order not to damage the tissue. For example, the pipe 124 of the pipe member 120 may be formed of a silicon material.

The pipe member 120 has flexibility and thus is not easy to move forward in the tissue of the living body. In order to solve this problem, the support member 110 of the insertion path forming unit 100 is inserted into the pipe member 120 to provide a desired level of stiffness to the pipe member 120.

The support member 110 includes the support rod 114 that elongates from a support unit 116 that extends in a longitudinal direction from a handle 112 of the support member 110 which an operator (or a surgeon) holds. A front end portion 118 is formed on the support rod 114 opposite to the handle 112.

In FIGS. 1 and 2, the insertion path forming unit 100 moves rightward in the tissue of the living body.

The support rod 114 of the support member 110 may be slidably inserted into the pipe 124 of the pipe member 120, and may be separated from the pipe 124 of the pipe member 120 when the operator pulls the handle 112 backward (leftward in FIGS. 1 and 2).

The pipe member 120 includes a coupling unit 122 including a mount groove 126 into which an insertion unit 108 protruding with a diameter less than that of the support unit 116 formed on the handle 112 of the support member 110 is inserted. An inner surface of the mount groove 126 is inclined as the mount groove 126 is tapered to change its diameter.

A shoulder portion protruding inward in a radial direction is formed on the inner surface of the mount groove 126 to receive any to-be-coupled member.

Accordingly, the front end portion 118 of the support member 110 passes through the mount groove 126 of the pipe member 120 and is disposed inside the pipe 124 not to pass through an inclined insertion unit 128 of the pipe member 120. In a state where the support member 110 is completely inserted into the pipe member 120, the front end portion 118 of the support member 110 extends substantially to the inclined insertion unit 128 of the pipe member 120 and supports the inclined insertion unit 128.

Figure 3A:
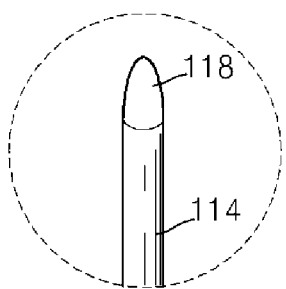
FIGS. 3A and 3B are enlarged views illustrating a portion A of FIG. 2, according to various embodiments of the present invention.
Figure 3B:
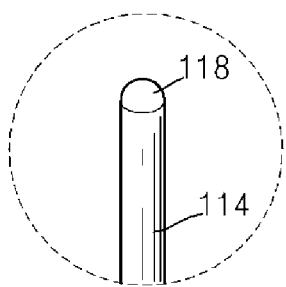

FIGS. 3A and 3B are enlarged views illustrating a portion A of FIG. 2, according to embodiments of the present invention.

Referring to FIG. 3A, the front end portion 118 of the support rod 114 of the support member 110 may be formed to have a partially oval cross-sectional shape. Referring to FIG. 3B, the front end portion 118 of the support rod 114 of the support member 110 may be formed to have a partially circular cross-sectional shape. Since the support rod 114 is inserted into the pipe 124 of the pipe member 120, an outer diameter of the support rod 114 may be the same as or less than an inner diameter of the pipe 124 of the pipe member 120.

FIGS. 4A through 4E are enlarged views illustrating the inclined insertion unit 128 when the pipe member 120 passes through the tissue of the living body, according to embodiments of the present invention.

Referring to FIGS. 4A through 4E, the inclined insertion unit 128 is formed on an end portion of the pipe 124 of the pipe member 120 to be tapered, and a two-step inclined portion 129 that is tapered at an angle greater than that of the inclined insertion unit 128 is formed on an end portion of the inclined insertion unit 128.

An outlet 127 which is hollow is formed at the center of the two-step inclined portion 129. A medical thread assembly including a medical thread and a support is discharged through the outlet 127. An inner diameter D1 of the outlet 127 has a size great enough for the medical thread assembly to pass through the outlet 127. The medical thread assembly is formed to have a size less than that of the inner diameter D1, and may pass through the outlet 127 while elastically expanding the outlet 127, instead of loosely passing through the outlet 127.

Figure 4A:
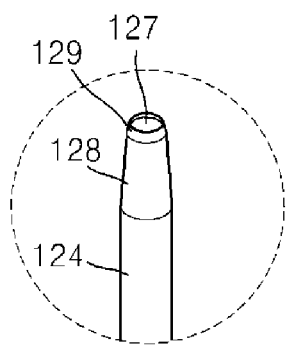
FIGS. 4A through 4E are enlarged views illustrating a portion B of FIG. 2, according to various embodiments of the present invention.
Figure 4A:
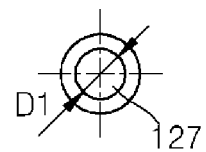
Figure 4B:
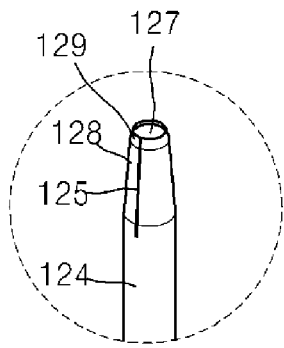
Figure 4B:
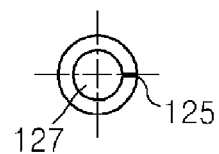

In FIG. 4A, in order for the medical thread assembly to pass through the outlet 127 while elastically expanding the outlet 127, no cut line is formed on the inclined insertion unit 128. However, in FIG. 4B, one cut line 125 is formed on the inclined insertion unit 128 in parallel to the longitudinal direction. Accordingly, when the medical thread assembly passes through and is discharged from the outlet 127, the inclined insertion unit 128 is curved along the cut line 125, thereby enabling the medical thread assembly to easily pass through and be discharged from the outlet 127.

Figure 4C:
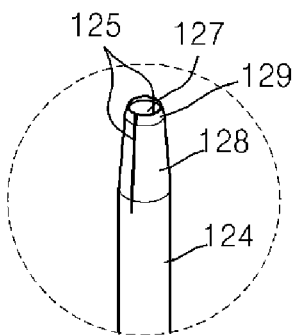
Figure 4C:
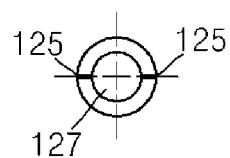
Figure 4D:
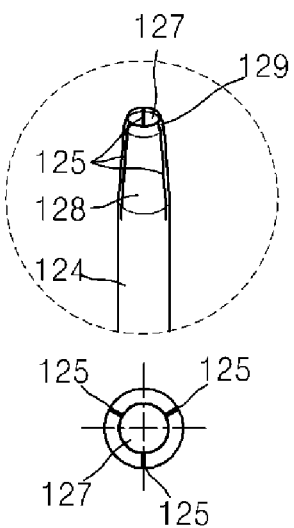
Figure 4E:
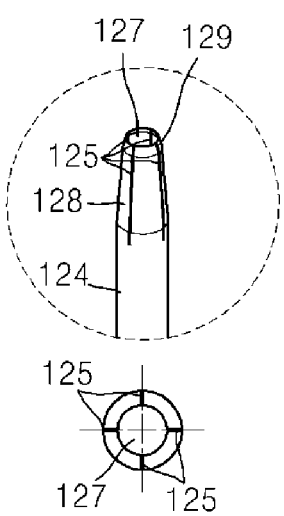

In FIG. 4C, two cut lines 125 are formed to face each other about the outlet 127. In FIG. 4D, three cut lines 125 are formed at intervals of 120° about the outlet 127. In FIG. 4E, four cut lines 125 are formed at intervals of 90° about the outlet 127.

Figure 5:
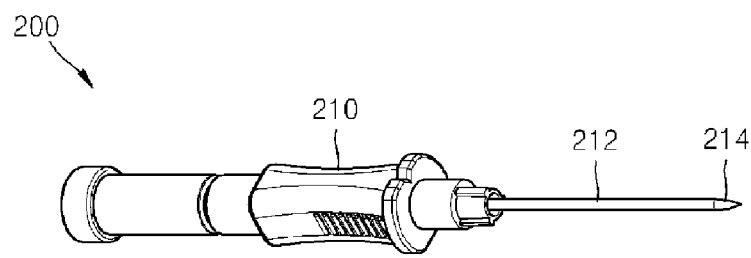
FIG. 5 is a perspective view illustrating a through-hole forming unit additionally disposed on the insertion path forming unit, according to an embodiment of the present invention.
Figure 6:
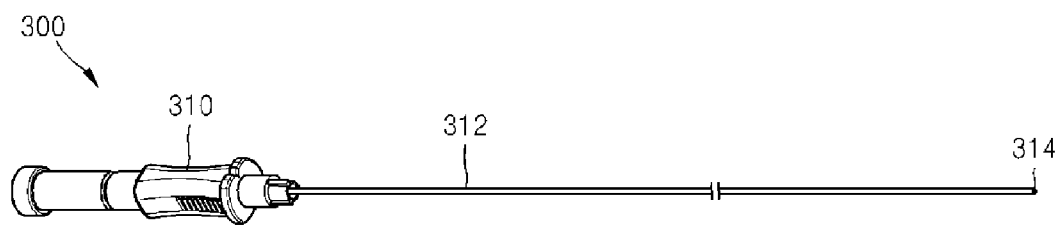
FIG. 6 is a perspective view illustrating a push unit according to an embodiment of the present invention.

FIG. 5 is a perspective view illustrating a through-hole forming unit 200 that constitutes a medical thread insertion surgery kit according to an embodiment of the present invention. The through-hole forming unit 200 is provided in order to mark a start position of the insertion path forming unit 100 and to secure a substantial movement path through which the insertion path forming unit 100 moves in the tissue.

The through-hole forming unit 200 includes a through-hole unit 214 that is formed on an end portion of a long through-hole rod 212 in order to form a through-hole in the tissue, and a handle 210 that is formed on an end portion of the through-hole rod 212 opposite to the through-hole unit 214.

The medical thread insertion surgery kit according to an embodiment of the present invention includes a push unit 300 for pushing the medical thread in a medical thread supply unit 400 (see FIG. 7A) coupled to the pipe member 120 after the support member 110 is removed from the insertion path forming unit 100 of FIG. 1.

The push unit 300 includes a handle 310 which the operator holds, a push rod 312 that extends from the handle 310, and a push unit 314 that is formed on an end portion of the push rod 312 and pushes the medical thread by contacting the medical thread.

The push rod 312 is formed to have a length great enough to pass through and stick out of the insertion path forming unit 100 and the medical thread supply unit 400.

Figure 7A:
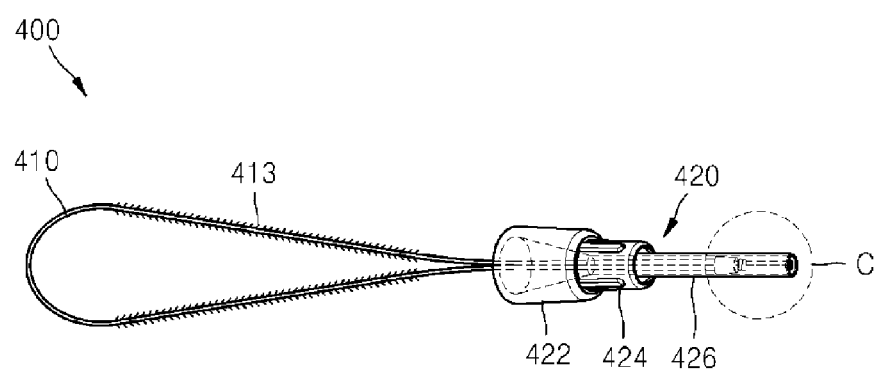
FIG. 7A is a perspective view illustrating a medical thread supply unit according to an embodiment of the present invention.
Figure 7B:
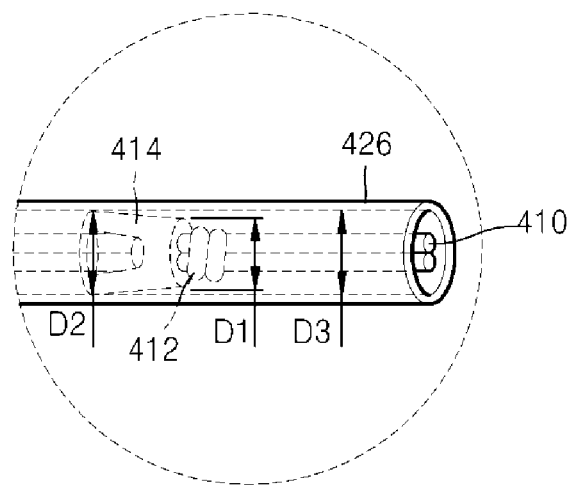
FIG. 7B is a partial enlarged view illustrating a portion C of FIG. 7A.

FIG. 7A is a perspective view illustrating the medical thread supply unit 400 that supplies the medical thread, according to an embodiment of the present invention. FIG. 7B is an enlarged view illustrating a portion C of FIG. 7A.

Referring to FIGS. 7A and 7B, the medical thread supply unit 400 is connected to the pipe member 120 after the support member 110 is removed in a state where the insertion path forming unit 100 is inserted into the tissue of the living body, a path through which the medical thread is inserted is secured, and the pipe member 120 is kept inserted into the tissue of the living body.

The pipe member 120 includes the coupling unit 122 including the mount groove 126 (see FIG. 2) to which the medical thread supply unit 400 is connected. The medical thread supply unit 400 includes a medical thread retaining unit 420 in which a medical thread 410 to be inserted is retained inside a supply pipe 426.

In this case, the medical thread retaining unit 420 includes a main body 422 on which a connector 424 having a complementary shape to the mount groove 126 of the pipe member 120 and coupled to the mount groove 126 is formed.

Referring to FIG. 7B, a medical thread support 414 for fixing the medical thread 410 in the tissue of the living body is formed on an end portion of the medical thread 410, and is disposed inside the supply pipe 426.

In the medical thread supply unit 400 of FIGS. 7A and 7B, the medical thread 410 has a loop shape and the medical thread support 414 is disposed at a position where both ends of the medical thread 410 are adjoined. In this case, the medical thread support 414 may have a truncated cone shape whose diameter increases away from a side where the medical thread 410 is inserted (right side in FIGS. 7A and 7B) toward an opposite side (left side in FIGS. 7A and 7B). That is, as shown in FIG. 7B, a diameter D1 of an end portion of the medical thread support 414 at a side where the medical thread 410 is inserted is less than a diameter D2 of an opposite end portion of the medical thread support 414, and an inner diameter D3 of the supply pipe 426 may be the same as or greater than the diameter D2 of the medical thread support 414.

In order to define a position of the medical thread support 414 in the supply pipe 426, a knot 412 is formed on an end portion of the medical thread 410 in a longitudinal direction of the medical thread 410.

Figure 8:
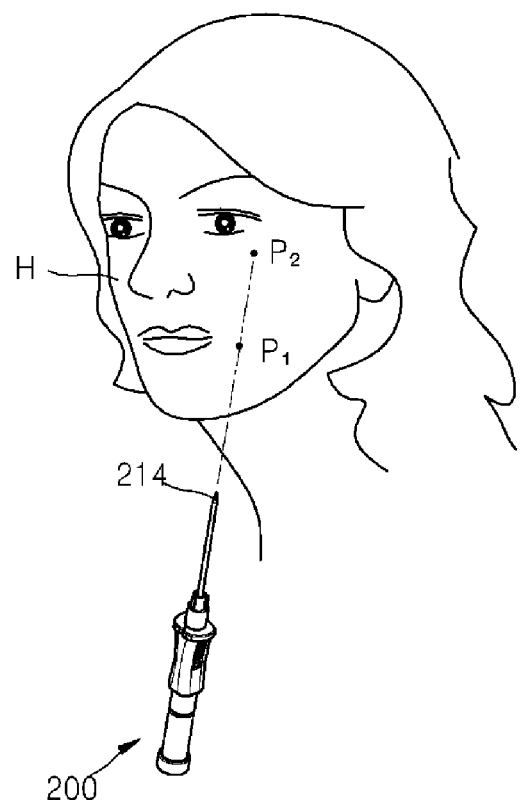
FIG. 8 is a schematic view for explaining how a through-hole is formed in the skin by using a medical thread insertion surgery kit including a medical thread insertion apparatus according to an embodiment of the present invention.

FIG. 8 is a perspective view illustrating a position P1 at which a medical thread is inserted into a face H and a position P2 at which the medical thread is fixed, according to an embodiment of the present invention. That is, a through-hole is formed by inserting the through-hole forming unit 200 at the position P1 where the medical thread is introduced into a tissue, and the medical thread is inserted into the tissue by the insertion path forming unit 100 inserted at the position P1, and is fixed to the tissue by the medical thread support 414 at the position P2.

FIGS. 9A through 9M are perspective views for explaining an order in which elements constituting a medical thread insertion surgery kit according to an embodiment of the present invention are used, in inserting a medical thread into the tissue of the living body by using the medical thread insertion surgery kit.

Figure 9A:
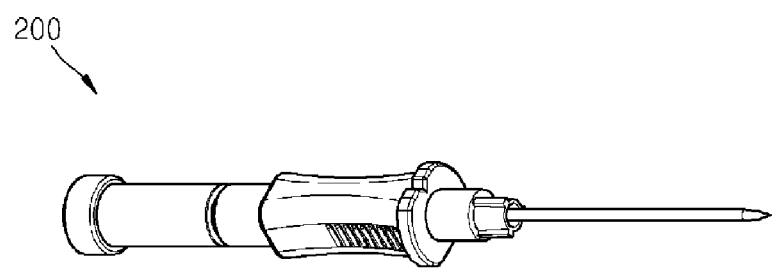
FIGS. 9A to 9M are schematic views for explaining a lift surgery using a medical thread insertion surgery kit including a medical thread insertion apparatus according to an embodiment of the present invention.
Figure 9B:
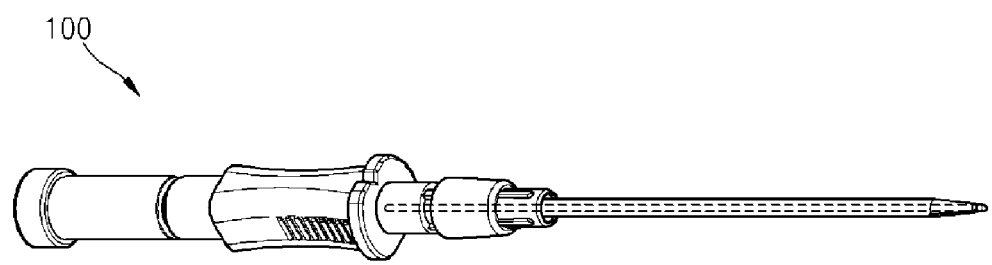

Referring to FIGS. 8 and 9A, a through-hole is formed at the position P1 of the living body by using the through-hole forming unit 200. Next, the operator introduces the insertion path forming unit 100 at the position P1 from which the through-hole forming unit 200 is taken out as shown in FIG. 9B. In a state where the support member 110 is coupled to the pipe member 120, the insertion path forming unit 100 is inserted into the tissue of the living body. In this case, since the pipe member 120 is flexible, it is not easy for the pipe member 120 to be introduced into the tissue. However, since the support member 110 having stiffness greater than that of the pipe member 120 is inserted into the pipe member 120 and acts as a frame of the pipe member 120, the insertion path forming unit 100 may be easily introduced substantially to the position P2 in the tissue.

Figure 9C:
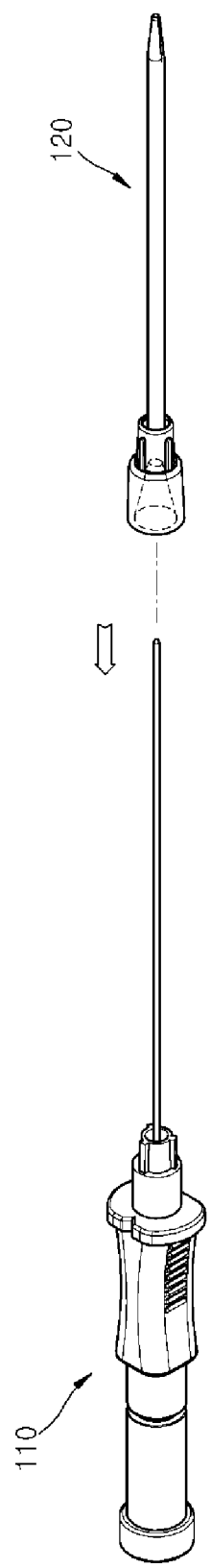

Referring to FIG. 9C, once an end portion of the insertion path forming unit 100 is introduced substantially to the position P2 of the tissue, the operator separates only the support member 110 backward from the insertion path forming unit 100 in a state where the pipe member 120 is inserted into the tissue.

Figure 9D:
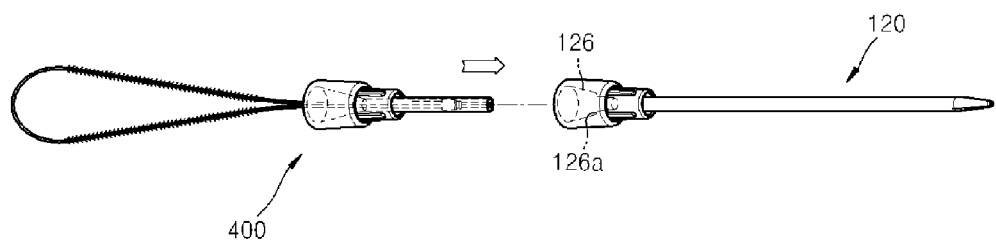
Figure 9E:
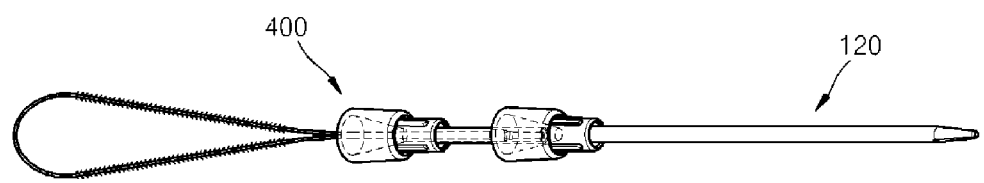

Referring to FIGS. 9D and 9E, the medical thread supply unit 400 is inserted into the pipe member 120 from which the support member 110 has been separated. In this case, since the shoulder portion 126a protruding inward in the radial direction is formed on the inner surface of the mount groove 126, when an end portion of the medical thread supply unit 400 is received in the mount groove 126 of the pipe member 120, an end portion of the supply pipe 426 (see FIG. 7A) is mounted on the shoulder portion 126a.

Figure 9F:
Figure 9G:
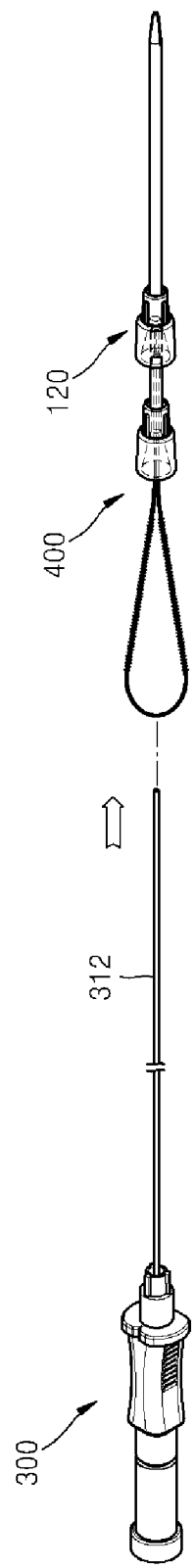
Figure 9H:
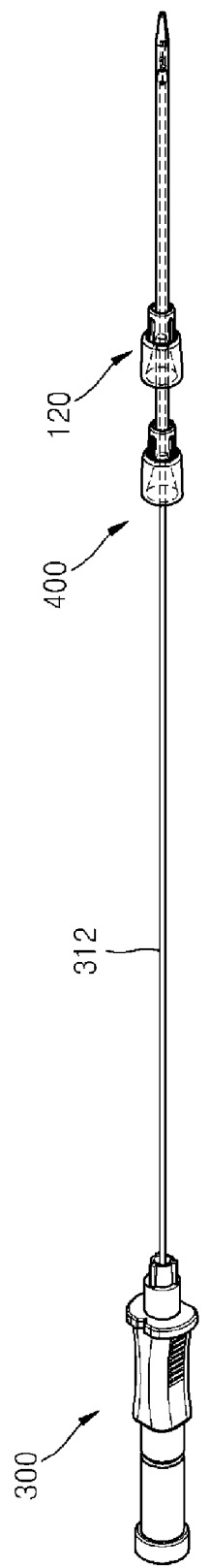

In a state where the medical thread supply unit 400 is coupled to the pipe member 120 of the insertion path forming unit 100, the push unit 300 is prepared as shown in FIG. 9F and the operator pushes the medical thread 410 of the medical thread supply unit 400 connected to the pipe member 120 from behind by using the push unit 300 as shown in FIGS. 9G and 9H.

Once the operator pushes the medical thread 410 of the medical thread supply unit 400 by using the push unit 300, the medical thread 410 passes through the supply pipe 426 of the medical thread supply unit 400, is guided into the pipe member 120 of the insertion path forming unit 100, and is discharged through the outlet 127 of the inclined insertion unit 128 formed on the end portion of the pipe member 120.

When the medical thread 410 is discharged through the inclined insertion unit 128 of the pipe member 120, the inclined insertion unit 128 may be curved such that a diameter of the inclined insertion unit 128 is increased to easily discharge the medical thread 410. For example, as shown in FIG. 9J, the diameter of the inclined insertion unit 128 is increased along cut lines formed on the inclined insertion unit 128, and the medical thread 410 and the medical thread support 414 are discharged through the outlet 127 of the inclined insertion unit 128 whose diameter has been increased.

Figure 9I:
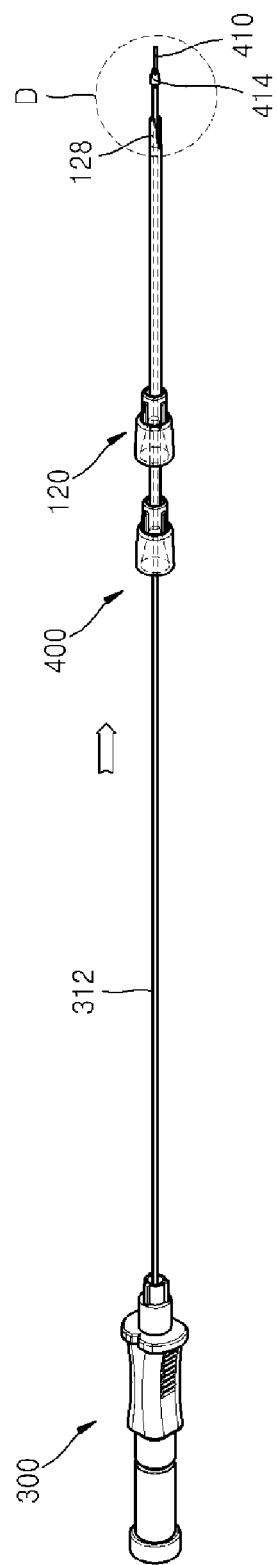
Figure 9J:
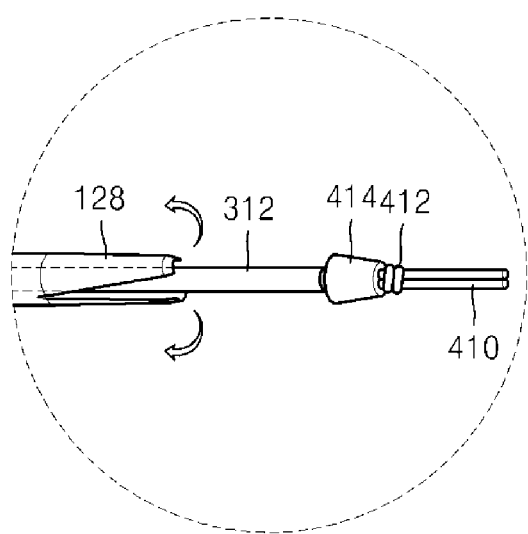
Figure 9K:
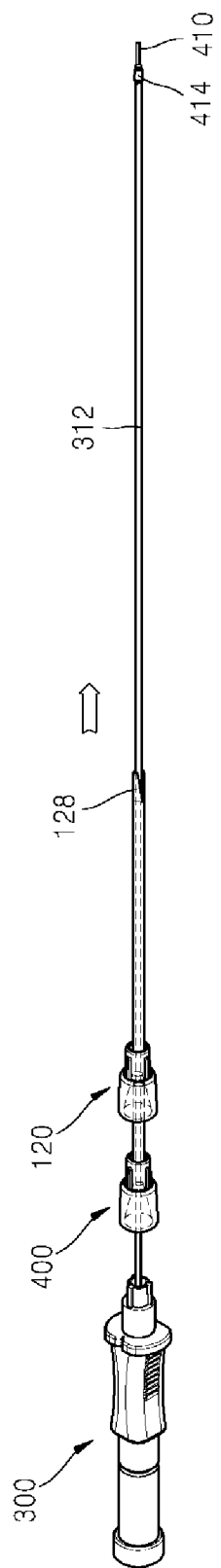

Referring to FIG. 9K, the operator additionally pushes the push unit 300 and accurately locates the medical thread support 414 of the medical thread 410 at a fixed position in the tissue. Since the medical thread support 414 has a truncated cone shape and may move only in one direction toward a smaller diameter, a position of the medical thread support 414 is determined by additionally pushing the push unit 300.

Once the medical thread support 414 reaches and is fixed to a predetermined position, as shown in FIG. 9I, the push unit 300, the medical thread supply unit 400, and the pipe member 120 of the insertion path forming unit 100 are moved backward to be taken out. Accordingly, the medical thread 410 is completely discharged from the inclined insertion unit 128 and is disposed in the tissue.

Figure 9L:
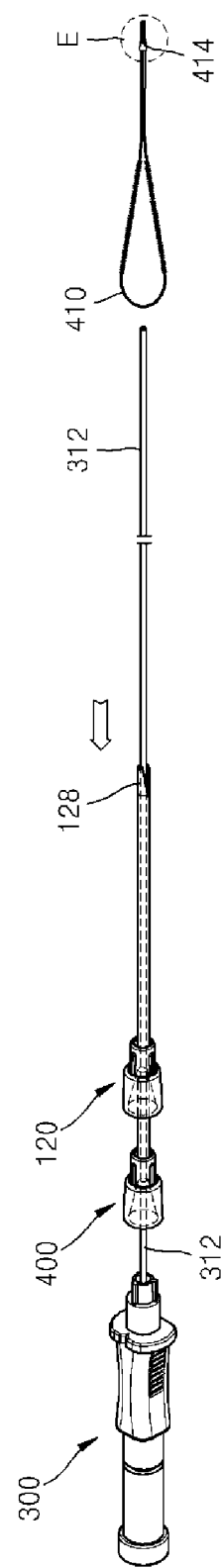
Figure 9M:
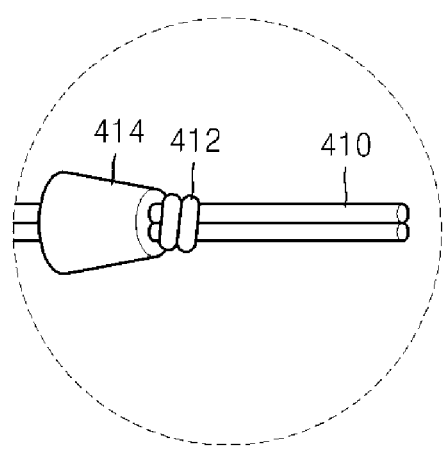
Figure 11A:
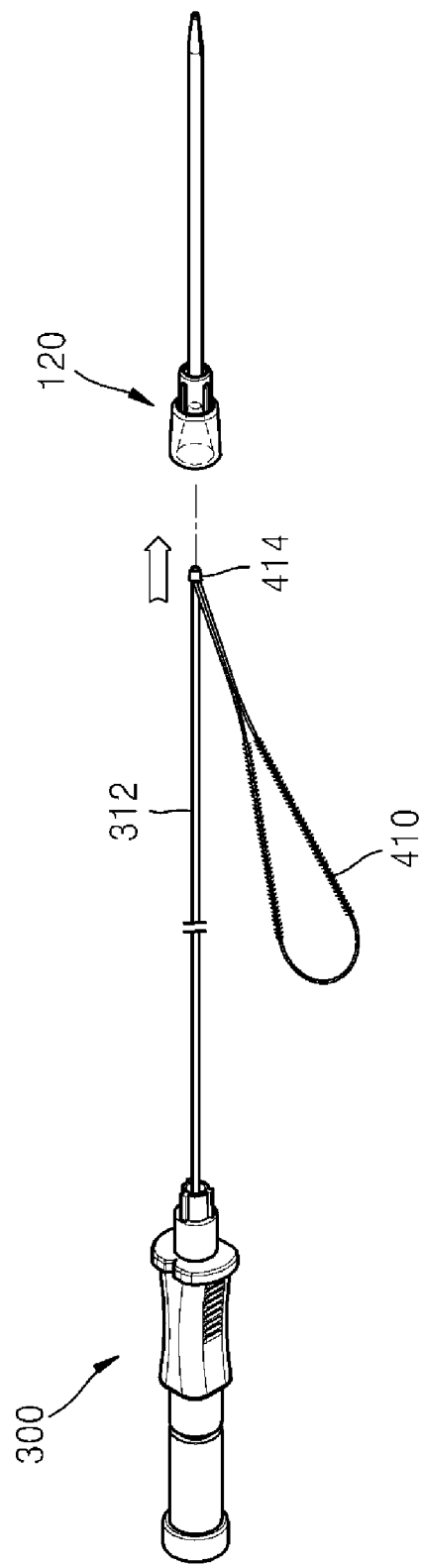
FIGS. 11A and 11B are schematic views for explaining some procedures of a lift surgery using a medical thread insertion surgery kit including a medical thread insertion apparatus according to another embodiment of the present invention.
Figure 11B:
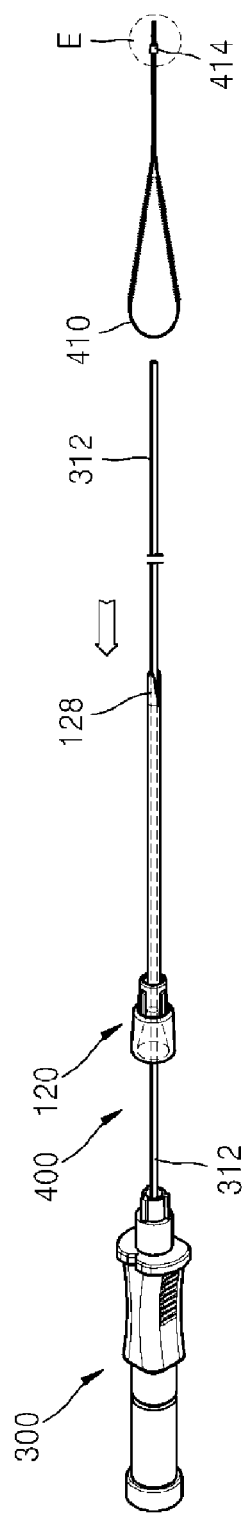

Referring to FIG. 9M which an enlarged view illustrating a portion E of FIG. 9L or 11B, the medical thread support 414 of the medical thread 410 is fixed to a predetermined point of the tissue due to its truncated cone shape, and barbs 413 formed on the medical thread 410 catch hold of the tissue. To this end, the medical thread 410 includes the barbs 413 that obliquely protrude toward an end portion of the medical thread 410 at a side where the medical thread 410 is inserted (right side in FIG. 9M).

Next, the operator adjusts a direction in which elasticity of the tissue of the living body is to be improved by pushing the tissue of the living body in a predetermined direction when the medical thread 410 is fixedly inserted.

The medical thread support of the medical thread may be formed of a non-absorbable material which is not absorbed into the living body, or an absorbable material as desired. For example, the medical thread support of the medical thread may be formed of, but is not limited to, nylon, polypropylene (e.g., polypropylene mesh), polyvinylidene fluoride, polyester, stainless steel, gold, titanium, silicon, medpore, gore-tex, mesh, polyactic acid, polydioxanone (PDO, PDS), or a copolymer of lactic acid and glycolic acid. When the medical thread support of the medical thread is formed of an absorbable material that may be absorbed into the living body, the medical thread support does not have to be removed after suture is performed in the living body.

A length of the medical thread support of the medical thread may range, for example, from about 1 mm to about 10 mm, but the present embodiment is not limited thereto and the length of the medical thread support may be adjusted according to where and why the medical thread support is used. A diameter of a front end of the medical thread support whose diameter is relatively small may range from about 0.1 mm to about 2 mm and a diameter of a rear end of the medical thread support whose diameter is relatively large may range from about 0.5 mm to about 5 mm, but the present embodiment is not limited thereto and the diameters may be adjusted according to a thickness and use of the medical thread.

One, two, three, or four or more medical threads with the barbs may be used, and the number of the medical threads may be appropriately adjusted according to a thickness and use of the medical threads, and each of the medical threads may be obtained by twisting or braiding a single strand or multiple strands.

The barbs may be arranged on the medical thread according to a desired configuration, and may be formed by using any of appropriate methods including well-known methods in the field. Examples of the well-known methods are injection molding using pressure, stamping, and cutting by knife or laser. A desired number of acute angular cuts are made by using the medical thread. A size of each of the barbs may be appropriately adjusted according to a use within the scope of the present invention. For example, a depth of each of the barbs 413 formed on the medical thread may range from about 30 microns ($\mu$) to about 100$\mu$, and may be adjusted according to a diameter of the medical thread. A distance between the barbs formed on the medical thread may range from about 100$\mu$ to about 1 mm, or more.

The medical thread may be formed of any of various materials, for example, a polymer material, a metal material, and a biological material. For example, the medical thread may be formed of, but is not limited to, a non-absorbable material such as polypropylene, gold, stainless steel, titanium, nylon, polyvinylidene fluoride, polyester, or braided silk, or an absorbable material such as polydioxanone (PDO, PDS).

Figure 10A:
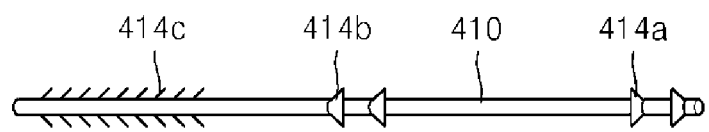
FIGS. 10A to 10C are side views of examples of a medical thread used in a medical thread insertion surgery kit including a medical thread insertion apparatus according to an embodiment of the present invention.
Figure 10B:
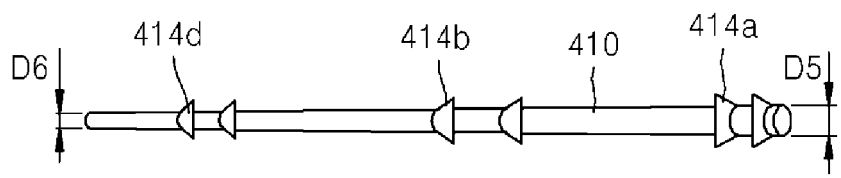

Instead of the medical thread assembly including the medical thread 410 and the medical thread support 414 used for the medical thread supply unit 400 of FIG. 7A, a medical thread assembly including the medical thread 410, supports 414a and 414b, and barbs 414c and 414d of FIGS. 10A and 10B may be used.

Referring to FIG. 10A, the medical thread 410 is linear and includes at least one support 414a having one orientation and a truncated cone shape, disposed on an end portion of the medical thread 410 at a side where the medical thread is introduced and a plurality of barbs 414c obliquely protruding toward the end portion of the medical thread 410 at a side where the medical thread is inserted (right side in the drawing), disposed on an opposite end portion of the medical thread 410, and a plurality of supports 414b having a truncated cone shape and an orientation opposite to that of the support 414a, disposed between the support 414a and the barbs 414c.

According to an alternative embodiment of the present invention, referring to FIG. 10B, the medical thread 410 is linear and includes at least one support 414a having one orientation and a truncated cone shape, disposed on an end portion of the medical thread 410 at a side where the medical thread is inserted, and instead of the barbs illustrated in FIG. 10A, one or more supports 414d and 414b having a truncated cone shape and an orientation opposite to that of the support 414a, disposed on the opposite end portion of the medical thread 410.

In this case, at the side where the medical thread 410 is introduced into the skin tissue, the medical thread 410 is required to have greater stiffness. Accordingly, a diameter (D5) of the medical thread 410 at the side where the medical thread 410 is introduced into the skin tissue may be greater than a diameter (D6) of the medical thread 410 at the opposite side.

Figure 10C:
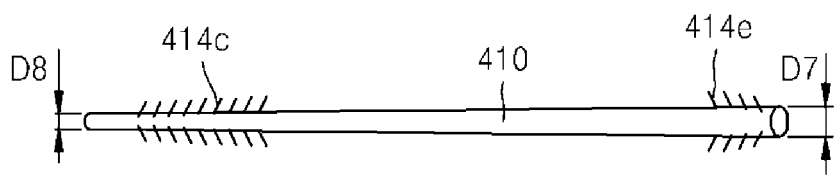

Optionally, as illustrated in FIG. 10C, instead of supports having a truncated cone shape, barbs 414c and 414e having one orientation may be disposed at both end portions of the medical thread 410.

Referring to FIG. 10C, barbs of the medical thread 410 formed on an end portion at the side where the medical thread 410 is introduced into the skin tissue include barbs 414e obliquely protruding toward the opposite side to the introduction side, and barbs 414d protruding obliquely in an orientation opposite to that of the barbs 414e are disposed on the opposite end portion of the medical thread 410.

In this case, like in FIG. 10B, at the side where the medical thread 410 is introduced into the skin tissue, the medical thread 410 is required to have greater stiffness. Accordingly, a diameter (D7) of the medical thread 410 at the side where the medical thread 410 is introduced into the skin tissue may be greater than a diameter (D8) of the medical thread 410 at the opposite side.

FIGS. 11A and 11B are views for explaining how a medical thread is inserted by using a medical thread insertion apparatus according to an embodiment of the present invention, and FIGS. 11A and 11B illustrate a modification of the embodiment explained in connection with FIGS. 9G and 9I.

Referring to FIGS. 11A and 11B, the medical thread supply unit 400 of the medical thread insertion apparatus is different from the medical thread supply unit 400 illustrated in FIGS. 9G and 9I. The medical thread supply unit 400 illustrated in FIGS. 11A and 11B includes the medical thread 410 and the medical thread support 414 that is disposed on an end portion of the medical thread 410 and is to fix a medical thread in the tissue of the living body. That is, the medical thread supply unit 400 according to the modified embodiment illustrated in FIGS. 11A and 11B is different from the medical thread supply unit 400 illustrated in FIG. 7A in that the medical thread retaining unit 420 is omitted.

Accordingly, referring to FIGS. 11A and 11B, the medical thread supply unit including the medical thread 410 and the medical thread support 414 disposed on the end portion of the medical thread 410 is inserted into and then separably fixed on an end of the push rod 312 of the push unit 300, and then, the push rod 312 allows the medical thread supply unit to be inserted into the pipe member 120 and pushes the medical thread 410.

While the present invention has been particularly shown and described with reference to exemplary embodiments thereof, it will be understood by those of ordinary skill in the art that various changes in form and details may be made therein without departing from the spirit and scope of the present invention as defined by the following claims. In particular, although a method of improving elasticity of a tissue of a living body of the present invention has been described by referring to a lift surgery (so called, facelift) for reducing wrinkles of a face skin, the present invention is not limited thereto. The method may be used for aesthetic enhancement to lift a loose skin or tissue and reduce wrinkles on any of various portions of bodies including human and non-human animal bodies, and may also be used for medical treatment to improve elasticity of a tissue of a living body. Accordingly, the technical scope of the present invention has to be defined by the appended claims.

INDUSTRIAL APPLICABILITY

The present invention may be useful for the technical field related to the medical operation.

What is claimed is:

1. A surgery kit comprising:
a support rod comprising a grip and an elongated body;
a hollow pipe extending between a first end and a second end, wherein the hollow pipe is configured to receive the support rod to form an assembly in which the grip is on the side of the first end of the hollow pipe and the elongated body is inside the hollow pipe, wherein the assembly is configured to be inserted through a hole formed on skin of a subject and move through tissues underneath the skin such that the second end of the hollow pipe reaches a target area underneath the skin and further such that, when the support rod is removed from the hollow pipe, the second end of the hollow pipe remains in the target area underneath the skin;
a suture device comprising a bio-absorbable body and a thread coupled to the bio-absorbable body, wherein the bio-absorbable body comprises a wider end and a narrower end that is narrower than the wider end, wherein the thread comprises a knot on the side of the narrower end and further comprises at least one strand extending from the wider end, wherein the thread further comprises a plurality of barbs projected from the at least one strand and inclined facing the bio-absorbable body such that an acute angle is formed between projection of the plurality of barbs from the at least one strand and extension of the at least one strand in a direction toward the bio-absorbable body at the projection from the at least one strand;
a suture supply device comprising a pipe-coupling end, a suture-receiving end and a hollow channel connecting between the pipe-coupling end and the suture-receiving end, wherein the pipe-coupling end of the suture supply device is configured to couple to the first end of the hollow pipe such that the hollow channel of the suture supply device and the hollow pipe are connected, wherein the suture-receiving end is configured to receive the suture device such that the entire portion of the bio-absorbable body is inserted into the hollow channel of the suture supply device with the narrower end facing the pipe-coupling end; and
a push rod configured to push the bio-absorbable body through the hollow channel of the suture supply device and further through the hollow pipe such that the bio-absorbable body travels through the hollow channel of the suture supply device and further through the hollow pipe to reach the target area underneath the skin.

2. The surgery kit of claim 1, wherein the hollow channel of the suture supply device has a diameter which is the same as or greater than that of the wider end of the bio-absorbable body.

3. The surgery kit of claim 1, wherein the plurality of barbs of the suture device are placed outside the hollow channel of the suture supply device when the entire portion of the bio-absorbable body is inserted into the hollow channel.

4. The surgery kit of claim 1, wherein the bio-absorbable body is in a truncated conical shape with the narrower end and the wider end.

5. The surgery kit of claim 1, wherein, the second end of the hollow pipe is tapered.

* * * * *

UNITED STATES PATENT AND TRADEMARK OFFICE
CERTIFICATE OF CORRECTION

PATENT NO. : 10,178,990 B2  
APPLICATION NO. : 14/648070  
DATED : January 15, 2019  
INVENTOR(S) : Young Jae Kim Page 1 of 1

It is certified that error appears in the above-identified patent and that said Letters Patent is hereby corrected as shown below:

On the Title Page

On Page 3, in the right column, at Line 8, change "%EE%" to --%ED%--.

On Page 3, in the right column, at Line 29, change "mfds.go.kr," to --mfds.go.kr/,--.

In the Specification

In Column 9, at Line 21, change "polyactic acid," to --polylactic acid,--.

Signed and Sealed this  
Twenty-eighth Day of May, 2019

Andrei Iancu  
*Director of the United States Patent and Trademark Office*